US009848945B2

(12) United States Patent
Goshayesshgar

(10) Patent No.: US 9,848,945 B2
(45) Date of Patent: *Dec. 26, 2017

(54) RF ENABLED INFLATABLE BONE TAMP

(71) Applicant: KYPHON SARL, Neuchatel (CH)

(72) Inventor: Mojan Goshayesshgar, Atherton, CA (US)

(73) Assignee: Kyphon SÀRL, Neuchâtel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/869,604

(22) Filed: Sep. 29, 2015

(65) Prior Publication Data

US 2016/0022354 A1    Jan. 28, 2016

Related U.S. Application Data

(63) Continuation of application No. 13/833,670, filed on Mar. 15, 2013, now Pat. No. 9,173,701.

(51) Int. Cl.
*A61B 18/12* (2006.01)
*A61B 18/14* (2006.01)
*A61B 18/00* (2006.01)
*A61B 17/70* (2006.01)
*A61B 17/88* (2006.01)

(52) U.S. Cl.
CPC ........ *A61B 18/148* (2013.01); *A61B 17/7097* (2013.01); *A61B 17/8855* (2013.01); *A61B 2018/0022* (2013.01); *A61B 2018/00023* (2013.01); *A61B 2018/00267* (2013.01); *A61B 2018/00565* (2013.01); *A61B 2018/00642* (2013.01); *A61B 2018/00791* (2013.01); *A61B 2018/00875* (2013.01)

(58) Field of Classification Search
CPC .............. A61B 18/148; A61B 17/7097; A61B 17/8855; A61B 2018/0023; A61B 2018/0022; A61B 2018/00267; A61B 2018/00565; A61B 2018/00642; A61B 2018/00791; A61B 2018/00875
USPC .................................. 606/41, 22, 34, 38, 45
See application file for complete search history.

(56) References Cited

U.S. PATENT DOCUMENTS

| | | | |
|---|---|---|---|
| 5,536,267 A | * | 7/1996 | Edwards ................. C22F 1/183 604/22 |
| 6,004,269 A | | 12/1999 | Crowley et al. |
| 6,056,744 A | | 5/2000 | Edwards |
| 6,254,598 B1 | | 7/2001 | Edwards et al. |
| 6,322,560 B1 | | 11/2001 | Garbagnati et al. |
| 6,506,189 B1 | | 1/2003 | Rittman, III et al. |

(Continued)

FOREIGN PATENT DOCUMENTS

WO    2012122157 A1    9/2012

OTHER PUBLICATIONS

International Search Report and Written Opinion for PCT/US2014/022569, the counterpart application mailed on Jun. 24, 2014.

*Primary Examiner* — Michael Carey

(57) ABSTRACT

A device for performing a surgical procedure includes an elongated shaft extending between a proximal end and a distal end. The shaft includes an outer surface and an inner surface. An expandable member is disposed at the distal end of the shaft. The expandable member is configured to receive inflation material. At least one electrode is disposed with the inflatable member. Methods of use are disclosed.

19 Claims, 3 Drawing Sheets

(56) References Cited

U.S. PATENT DOCUMENTS

| | | |
|---|---|---|
| 6,780,183 B2 | 8/2004 | Jimenez et al. |
| 7,184,811 B2 | 2/2007 | Phan |
| 7,371,232 B2 | 5/2008 | Scheib |
| 7,959,631 B2 | 6/2011 | Dicarlo |
| 8,192,442 B2 | 6/2012 | Truckai et al. |
| 9,173,701 B2 * | 11/2015 | Goshayeshgar ..... A61B 18/148 |
| 2001/0034518 A1 | 10/2001 | Edwards et al. |
| 2003/0163126 A1 * | 8/2003 | West, Jr. .......... A61B 17/32002 606/41 |
| 2003/0236455 A1 | 12/2003 | Swanson et al. |
| 2004/0167509 A1 | 8/2004 | Taimisto |
| 2005/0096647 A1 | 5/2005 | Steinke et al. |
| 2005/0288730 A1 | 12/2005 | Deem et al. |
| 2006/0122614 A1 | 6/2006 | Truckai et al. |
| 2007/0129720 A1 | 6/2007 | Demarais et al. |
| 2012/0022574 A1 | 1/2012 | Mafi et al. |
| 2012/0029509 A1 * | 2/2012 | Smith ................ A61B 18/1492 606/41 |
| 2012/0029511 A1 | 2/2012 | Smith et al. |
| 2012/0053611 A1 | 3/2012 | Saab et al. |
| 2012/0130363 A1 | 5/2012 | Kim et al. |
| 2013/0296855 A1 | 11/2013 | Sigmon, Jr. |
| 2014/0031810 A1 * | 1/2014 | Mahvi ................... A61B 18/18 606/33 |
| 2014/0236144 A1 | 8/2014 | Krueger et al. |
| 2014/0276728 A1 | 9/2014 | Goshayeshgar |

\* cited by examiner

RF ENABLED INFLATABLE BONE TAMP

CROSS-REFERENCE TO RELATED APPLICATIONS

This application is a continuation of U.S. patent application Ser. No. 13/833,670, filed Mar. 15, 2013, which is hereby incorporated by reference herein in its entirety.

TECHNICAL FIELD

The present disclosure generally relates to medical devices for the treatment of cancers, and more particularly to a surgical system and method employing an inflatable bone tamp to correct vertebral deformities, ablate tumors and stabilize fractures in cancer patients.

BACKGROUND

Radio frequency ablation (RFA) is a medical procedure in which tumors or other dysfunctional tissue is ablated using the heat generated from high frequency alternating current. An important advantage of radio frequency (RF) current (over previously used low frequency AC or pulses of DC) is that RF current does not directly stimulate nerves or muscles and can therefore often be used without the need for general anesthetic. RFA has become increasingly accepted in the last 15 years with promising results. RFA procedures are performed under image guidance (such as X-ray screening, CT scan or ultrasound) by an interventional pain specialist (such as an anesthesiologist), interventional radiologist, a gastrointestinal or surgical endoscopist, or a cardiac electrophysiologist, a subspecialty of cardiologists.

RFA is performed to treat tumors in the lungs, liver, kidneys, bones and other organs. Once the diagnosis of tumor is confirmed, a needle-like RFA probe is placed inside the tumor. RF waves are passed through a probe to increase the temperature within tumor tissue to destroy the tumor. Generally, RFA is used to treat patients with small tumors that started within a specific organ (primary tumors) or that spread to the organ (metastases). The suitability of a patient to receive RFA is typically decided by doctors based on multiple factors. RFA can usually be administered as an out-patient procedure, but may at times require a brief hospital stay. RFA may be combined with locally-delivered chemotherapy to treat hepatocellular carcinoma (primary liver cancer). The low-level heat (hyperthermia) created by the RFA probe causes heat-sensitive liposomes to release concentrated levels of chemotherapy in margins around ablated tissue, which is a method commonly used to treat Hepatocellular carcinoma (HCC). RFA is also used in pancreatic cancer and bile duct cancer.

SUMMARY

In one embodiment, in accordance with the principles of the present disclosure, a device for performing a surgical procedure is provided comprising a cannula extending between a proximal end and a distal end. The cannula includes an outer surface and an inner surface. A balloon is disposed at the distal end of the cannula. The balloon is configured to receive inflation material and includes an inner surface defining a cavity. At least one electrode disposed with the balloon.

In one embodiment, in accordance with the principles of the present disclosure, a device for destroying pathological tissue is provided comprising a cannula extending between a proximal end and a distal end. The cannula includes an outer surface and an inner surface. A balloon is disposed at the distal end of the cannula. The balloon is configured to receive inflation material and includes an inner surface defining a cavity. At least one RF electrode is disposed with the balloon. A temperature feedback system is configured to monitor tissue desiccation.

In one embodiment, in accordance with the principles of the present disclosure, a method for destroying pathological tissue at a surgical site is provided. The method comprises providing a device comprising: a cannula extending between a proximal end and a distal end, the cannula including an outer surface and an inner surface; a balloon disposed at the distal end the cannula configured to receive inflation material, the balloon including an inner surface defining a cavity; at least one electrode disposed with the balloon and configured for emitting RF signals; and a temperature feedback system configured to monitor the extent of tissue desiccation; creating an access path to the surgical site; inserting the balloon into the surgical site and inflating the balloon; manipulating the balloon to move bone and create a void; emitting RF signals through the electrodes to thermally ablate and destroy pathological tissue; and monitoring the extent of tissue desiccation to determine if application of RF energy should be continued.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
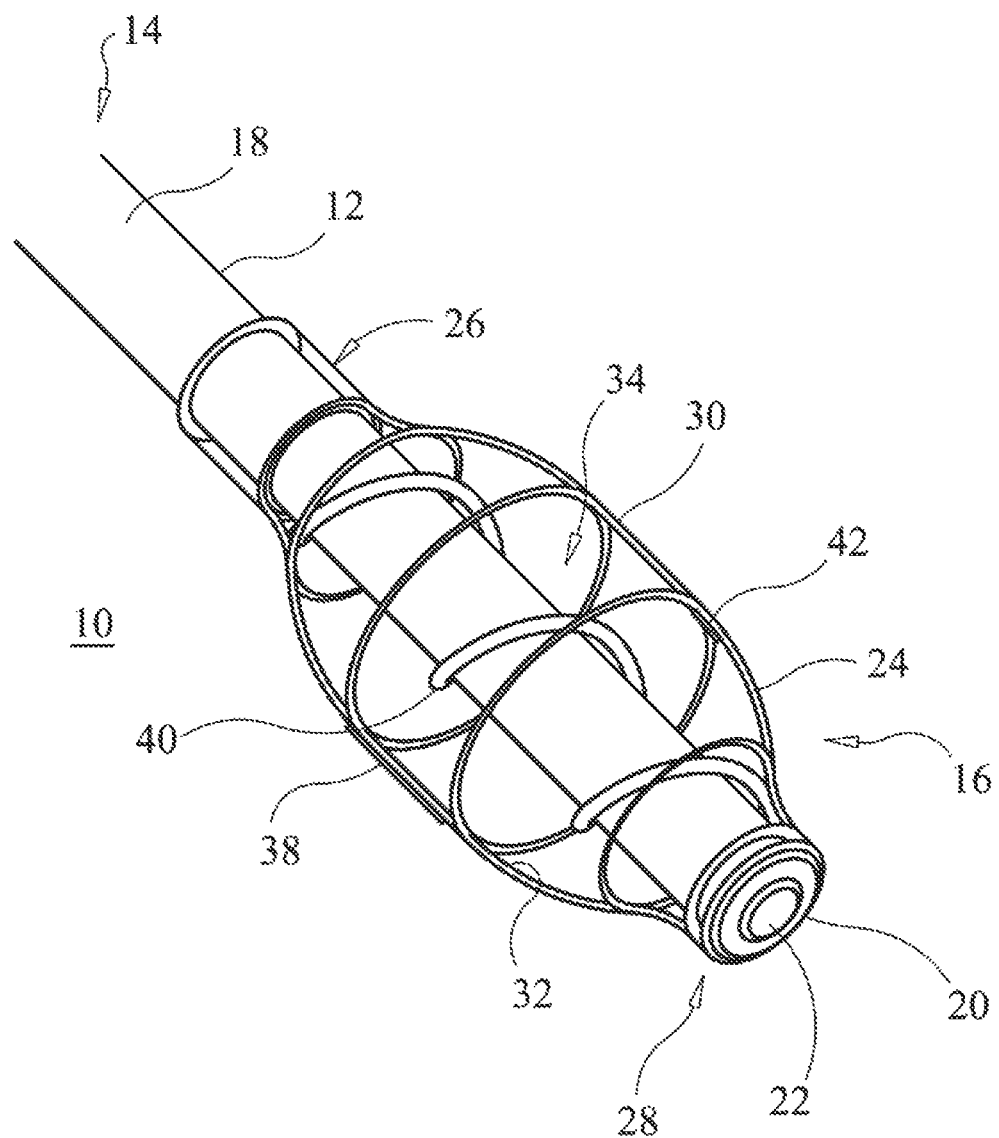
FIG. 1 is a perspective view of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system 10 and method for nerve destruction.

In one embodiment, an RF enable inflatable bone tamp is manipulated to move bone and create a void. RF energy is delivered to thermally ablate and destroy pathological tissue. The void is then filled according to the particular surgical procedure. The RF electrodes can be energized with either monopolar or bipolar RF. Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to surrounding normal tissue. Excessive temperatures can cause adverse tissue effects. During the course of heating, tissue in an overly-heated area may become desiccated and charred. As tissue temperature increases to 100° C., tissue will lose water content due to evaporation or by the diffusion of liquid water from treated cells, and the tissue becomes desiccated. Desiccation of the tissue changes the electrical and other material properties of the tissue, and may impede treatment. For example, as the tissue is desiccated, the electrical resistance of the tissue increases, making it increasingly more difficult to supply power to the tissue. Desiccated tissue may also adhere to the device, hindering delivery of power. At tissue temperatures in excess of 100° C., the solid contents of the tissue begin to char. Like desiccated tissue, charred tissue is relatively high in resistance to current and may impede treatment. In one embodiment, a temperature or impedance-based feedback system enables the system to accurately monitor the extent of tissue desiccation and permit continued delivery of the RF energy.

The RF enabled inflatable bone tamp includes one or a plurality of RF electrodes. The electrodes can be straight, helical or curved. The electrodes can be positioned inside, outside or within the wall of the RF enabled inflatable bone tamp. In one embodiment, a liquid pumping system may be connected to the RF enabled inflatable bone tamp to inflate and cool down inflation liquid used to inflate the RF enabled inflatable bone tamp dynamically (active cooling) or the RF enabled inflatable bone tamp may be inflated with a cooled liquid (passive cooling).

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, inflatable members (balloons) that are preformed to have different sizes and shapes.

It is envisioned that the present disclosure may be employed to treat bones, and in particular arm bones such as a distal radius. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference.

The components of system 10, individually or collectively, may also be fabricated from a heterogeneous material such as a combination of two or more of the above-described materials. The components of system 10 may be monolithically formed, integrally connected or include fastening elements and/or instruments, as described herein.

Figure 2:
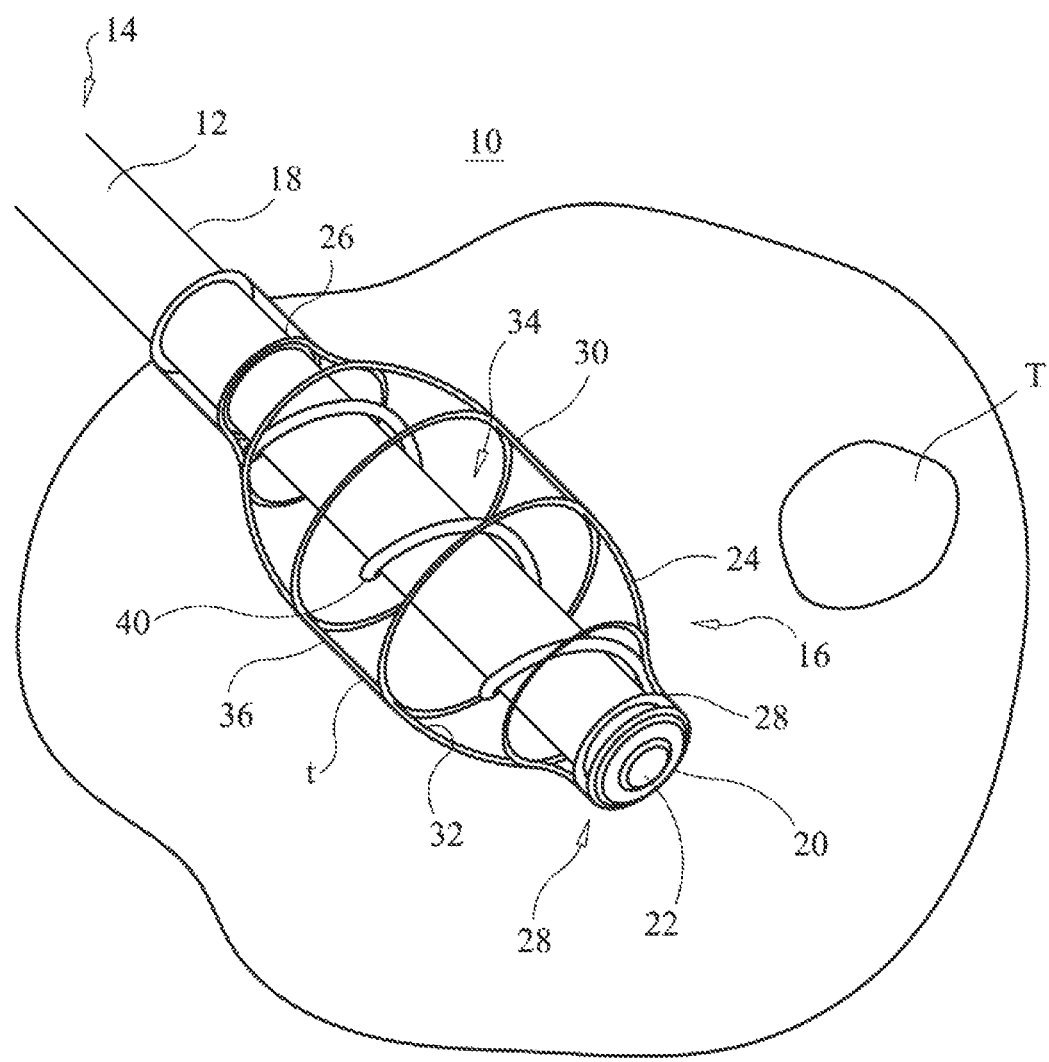
FIG. 2 is a perspective view of the system shown in FIG. 1 disposed in tissue.
Figure 3:
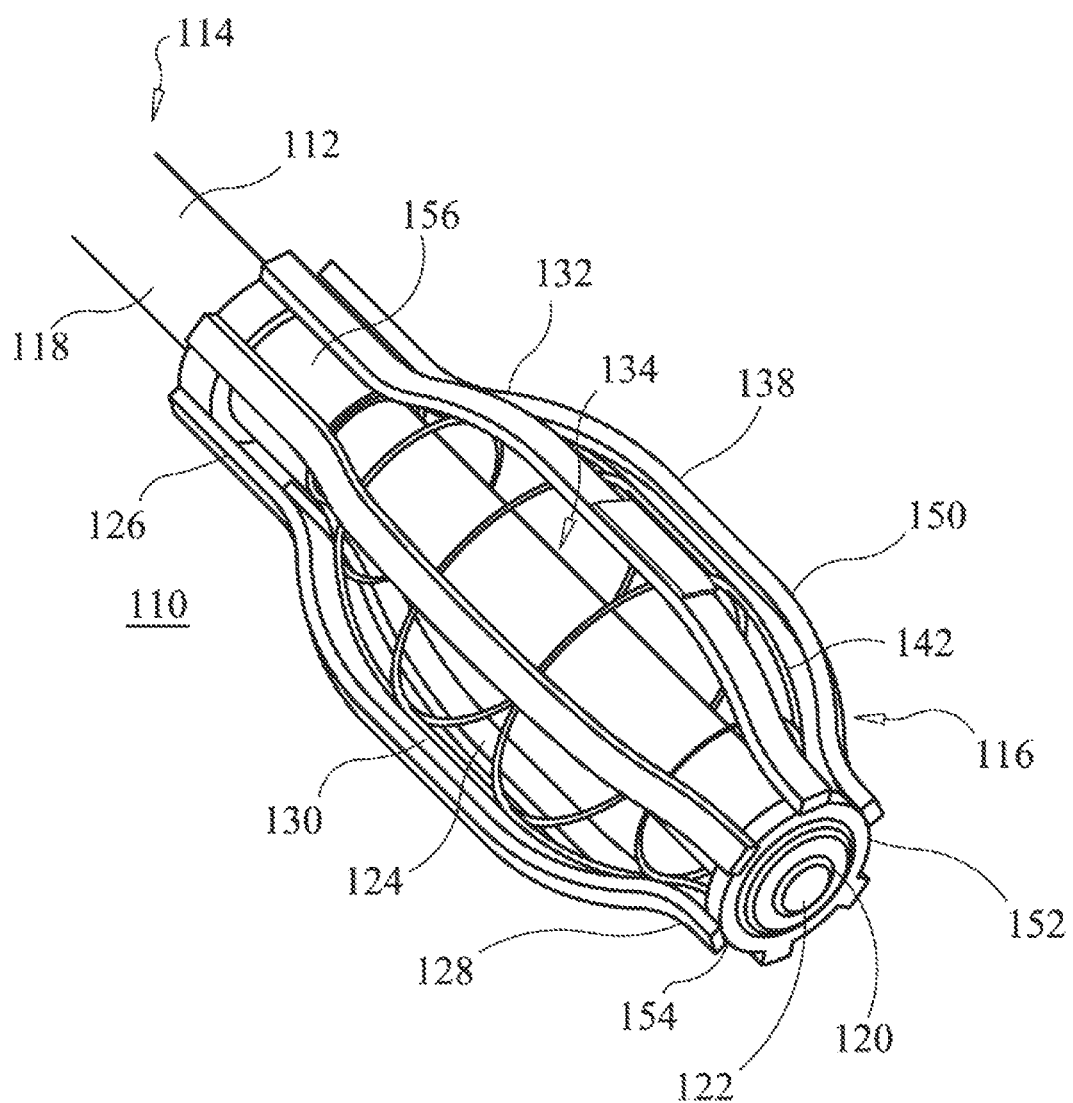
FIG. 3 is a perspective view of one embodiment of a surgical system in accordance with the principles of the present disclosure.

The following discussion includes a description of a system for performing a surgical procedure and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there are illustrated components of system 10 in accordance with the principles of the present disclosure.

As shown in FIGS. 1 and 2, system 10 includes an elongated shaft 12. Shaft 12 extends between a proximal end 14 and a distal end 16. Shaft 12 includes an outer surface 18 and an inner surface 20 defining a passageway 22. Passageway 22 extends the entire length of shaft 12 and has a cylindrical cross sectional configuration having a uniform diameter along the length of passageway 22. In some embodiments, passageway 22 may have alternate cross section configurations, such as, for example, oval, oblong, triangular, square, hexagonal, polygonal, irregular, uniform, non-uniform and/or tapered.

An inflatable member, such as, for example, a balloon 24 is disposed with distal end 16 of shaft 12. Balloon 24 has a proximal end 26 and a distal end 28. Balloon 24 includes an outer surface 30 and an inner surface 32. Surface 32 defines a cavity 34 extending the entire length of balloon 24. Balloon 24 includes a wall 36 extending between surfaces 30 and 32 and defines a thickness t. Shaft 12 may be attached to a fill tube (not shown) such that a material, such as, for example, saline, a contrast solution or compressed air may be delivered from the tube, through passageway 22 and into cavity 34. As the material fills cavity 34, balloon moves from an unexpanded configuration, to an expanded configuration. It is envisioned that the shapes and sizes of balloon 24 when in the expanded configuration can be selected to provide a desired result during a procedure. For example, balloon 24 may include shapes such as spheres, cylinders, etc. and have different dimensions to make balloon 24 narrower or wider in a longitudinal direction, or extend further in a radial direction. Balloon 24 comprises a compliant material, such as, for example, polyurethane, pellethane, polyethylene, silicone, cronoprene or non-compliant material such as Nylon.

It is envisioned that balloon 24 can be a single or multi-layered balloon where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation or expansion. For other applications, it will be apparent that one can vary size, material, and/or orientation to at least some degree, depending upon the requirements of a particular application.

It is contemplated that balloon 24 may include an impenetrable structural layer having low friction surfaces so as to facilitate deployment through a delivery tube, such as, for example, through shaft 12 and prevent rupture of balloon 24 as it is inflated or expanded in situ. Further variations are contemplated involving different combinations of lubricating layers and structural layers. In some embodiments, structural layers of balloon 24 can contain polyamides, polyesters, polyethylenes, polyurethanes, their co-polymers and combinations thereof.

At least one electrode 38 is disposed with balloon 24. Electrode 38 is configured to emit an RF frequency for cutting and/or destroying tissue or nerves. In one embodiment, shown in FIG. 1, electrode 38 is disposed on outer surface 30. In one embodiment, electrode 38 is disposed on inner surface 32. In one embodiment, electrode 38 is disposed within wall 26. This configuration will accommodate different anatomies as well as different control methods. Electrode 38 can be of any shape such as, for example, straight, helical or curved. If more than one electrode 38 is provided, they can be positioned symmetrically or directionally along balloon 24. The RF signal is configured to temporarily interrupt or destroy nerves to reduce pain in the patient.

In one embodiment, a temperature or impedance-based feedback system is provided. A sensor 42 of the feedback system is disposed on balloon 24 and is configured to monitor the temperature of tissue effected by the RF signal to determine the extent of desiccation and thereby determine if RF energy needs to be continued.

In one embodiment, a cooling mechanism is provided and is configured to cool inflation material used to move balloon 24 from the unexpanded configuration to the expanded configuration. In one embodiment, shown in FIG. 1, active cooling is providing by the cooling mechanism by including a cooling tube 40 disposed in within cavity 34. Cooling tube 40 extends thought shaft 12 and is connected to a liquid pumping system (not shown). In one embodiment, cooling tube 40 is disposed within wall 36 of balloon 24. As shown in FIG. 1, cooling tube 40 can spiral around shaft 12 such that cooling of the inflation material is uniform. In one embodiment, passive cooling is providing by having the cooling mechanism cool the inflation material prior to filling balloon 24.

In some embodiments, shaft 12 and/or balloon 24 includes one or a plurality of marker bands (not shown) comprising a radiopaque material. In one embodiment, the polymeric material is polyether block amide. In some embodiments, the highly radiopaque material incorporated into the polymeric material is barium sulfate, bismuth subcarbonate, tungsten, or a combination thereof.

In assembly, operation and use, system 10 is employed with a surgical procedure, such as, for a treatment of a cancerous tumor. It is contemplated that one or all of the components of system 10 can be delivered or implanted as a pre-assembled device or can be assembled in situ. System 10 may be completely or partially revised, removed or replaced. It is envisioned that system 10 may also be used to treat other affected portions of the patient, such as, for example, a calcaneus bone, bones of the feet or hands, bones of the spine, bones of the arms and legs, etc.

In use, to treat cancer, the medical practitioner obtains access to a surgical site including in any appropriate manner, such as through the skin, or through an incision and retraction of tissues. In one embodiment, a drill is employed to remove bone tissue to provide access to a repair site. It is envisioned that system 10 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 10 is determined according to the configuration, dimension and location of a selected section of nerves and the requirements of a particular application.

An incision is made in the body of a patient and a cutting instrument (not shown) creates a surgical pathway for implantation of components of system 10. This may include the use of a cannula or other device. A preparation instrument (not shown) can be employed to prepare tissue surfaces, as well as for aspiration and irrigation of a surgical region according to the requirements of a particular surgical application.

An instrument, such as, for example, a cannula may be inserted through the incision such that a distal end of the cannula is positioned adjacent the surgical site. Balloon 24 is then inserted through the cannula such that distal end 16 of balloon 24 is positioned adjacent the surgical site. A material, such as, for example, saline, a contrast solution or compressed air may be delivered through shaft 12 and passageway 22 and into cavity 34. The material may be delivered into cavity 34 until balloon 24 assumes the desire profile. Balloon 24 can be manipulated to move bone and create a void at the desired location by viewing balloon 24 with use of markers. As shown in FIG. 2, once balloon 24 is properly positioned within an organ or bone, electrode(s) 38 can be activated to emit the desired RF signal to heat the cancerous tissue T. Sensor 42 monitors the temperature of tissue T to determine the extent of desiccation and thereby determine if RF energy needs to be continued to further remove cancerous tissue. As RF signals are emitted, temperature of balloon 24 increases. The cooling mechanism may be utilized to decrease the temperature of balloon 24 so that the procedure can be repeated at various locations. Removal of the material from cavity 34 causes balloon 24 to move from the expanded configuration to the unexpanded configuration for removal from the patient. That is, after balloon 24 is moved from the expanded configuration to the unexpanded configuration, balloon 24 may be retracted into the cannula and removed.

As shown in FIG. 3, a balloon system 110 is provided in accordance with the principles of the present disclosure. System 110 includes an elongated shaft 112. Shaft 112 extends between a proximal end 114 and a distal end 116. Shaft 112 includes an outer surface 118 and an inner surface 120. Surface 120 defines a passageway 122. A balloon 124 is provided at distal end 116 of shaft 112. Balloon 124 has a proximal end 126 and a distal end 128. Balloon 124 includes an outer surface 130 and an inner surface 132. Surface 132 defines a cavity 134 extending the entire length of balloon 124. Cavity 134 is configured to receive an inflation material.

An expandable cage 150 is disposed around balloon 124. Cage 150 provides a certain amount of stiffness to balloon 124 and protects balloon 124 from bone material that may puncture balloon 124. In one embodiment, an electrode 138 similar to electrode 38 and a sensor 142 similar to sensor 42 are disposed with cage 150. Some advantages of using cage 150 includes ease of manufacturing and robustness of the device. In addition cage 150 also contributes to more accurate control in both temperature and impedance control modes. Cage 150 is configured to expand with balloon 124 as surface 130 of balloon 124 applies force to cage 150. As discussed above, a cooling mechanism, such as, for example, a cooling tube 140 is provided and is configured to cool inflation material used to move balloon 124 from an unexpanded configuration to an expanded configuration.

In one embodiment, a distal end 152 of the expandable cage 150 is attached to a ring-shaped member 154 having an inner surface defining an opening. Distal end 152 of cage 150 is positioned within the opening of ring shaped member 154. A proximal end of cage 150 is engaged with a collar 156 so that when balloon 124 expands, cage 150 expands. Similarly, when balloon 124 is deflated cage 150 contracts to give a slimmer profile.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The balloon can be modified or extended to accommodate particular formulations of balloon construction materials or fabrication techniques. Different balloon materials and surface coatings, or outer layers of different materials or surface coatings may also be applied to the balloon to facilitate a smaller balloon profile, biocompatibility, lubrication as well as other properties. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A surgical system configured for performing a surgical procedure to ablate pathological tissue at a surgical site in a patient comprising:

a cannula having a central longitudinal axis;

an inflatable bone tamp comprising at least one electrode disposed with the inflatable bone tamp, said electrode adapted to emit RF energy having a frequency sufficient for ablating the pathological tissue at the surgical site, the inflatable bone tamp including an expandable cage, the expandable cage including at least a first elongated member, a second elongated member, and a third elongated member, the first and second elongated members being spaced entirely apart from one another by a first gap in the expandable cage, the second and third elongated members being spaced entirely apart from one another by a second gap in the expandable cage, the first, second, and third elongated members each including an outer surface, an inner surface, and two side surfaces between the outer and inner surfaces, each of the outer surfaces, the inner surfaces, and the side surfaces having widths at least substantially perpendicular to the central longitudinal axis of the cannula, the widths of the outer surfaces and inner surfaces being substantially greater than the widths of the side surfaces;

a sensor to monitor the temperature of the pathological tissue effected by the RF energy;

a cutting instrument to create a surgical pathway for implantation of the inflatable bone tamp; and a liquid pumping system configured to be connected to the inflatable bone tamp.

2. A surgical system as recited in claim 1, wherein the inflatable bone tamp further comprises a spiral cooling tube configured to receive a cooling medium.

3. A surgical system as recited in claim 1, wherein the sensor is provided on the inflatable bone tamp to determine an amount of ablation of at least one of the pathological tissue and the surrounding non-pathological tissue.

4. A surgical system as recited in claim 1, further comprising an inflation material.

5. A surgical system as recited in claim 1, wherein the at least one electrode is configured to be energized by monopolar RF.

6. A surgical system as recited in claim 1, wherein tile at least one electrode is configured to be energized by bipolar RF.

7. A surgical system as recited in claim 1, wherein the at least one electrode is disposed on an exterior portion of the expandable cage.

8. A surgical system as recited in claim 1, wherein the system is disposable, placed in a peel-pack, or sterilized.

9. A surgical system as recited in claim 1, further comprising a drill.

10. A method of using a surgical system as recited in claim 1, the method comprising:

creating an access path to the surgical site;

inserting the inflatable bone tamp into the surgical site and inflating with an inflation material;

manipulating tile inflatable bone tamp to move bone and create a void;

emitting RF signals through the at least one electrode to thermally ablate and desiccate the pathological tissue;

monitoring desiccation of the pathological tissue to determine if application of RF energy should be continued;

providing a cooling medium into the inflatable bone tamp to uniformly decrease temperature;

deflating the inflatable bone tamp.

11. A method as recited in claim 10, wherein providing the cooling medium comprises providing the cooling medium to a spiral cooling tube within the inflatable bone tamp.

12. A method as recited in claim 10, further comprising monitoring the desiccation of the surrounding non-pathological tissue to determine if application of RF energy should be continued.

13. A method as recited in claim 10, further comprising cooling tile inflation material.

14. A method as recited in claim 10, wherein the system further comprises a drill, the method further comprises using the drill to remove tissue to gain access to the surgical site.

15. A method as recited in claim 10, further comprising aspirating or irrigating a surgical site.

16. A surgical system configured for performing a surgical procedure to ablate pathological tissue at a surgical site in a patient comprising:

at least one cannula;

at least one inflatable bone tamp comprising at least one electrode disposed with the inflatable bone tamp, said at least one electrode adapted to emit RF energy having a frequency sufficient for ablating the pathological tissue at the surgical site, the inflatable bone tamp including an expandable cage, the expandable cage including at least a first elongated member, a second elongated member, and a third elongated member, the first and second elongated members being spaced entirely apart from one another by a first gap in the expandable cage, the second and third elongated members being spaced entirely apart from one another by a second gap in the expandable cage, the first, second, and third elongated members each including an outer surface, an inner surface, and two side surfaces between the outer and inner surfaces, each of the outer surfaces, the inner surfaces, and the side surfaces having widths at least substantially perpendicular to the central longitudinal axis of the cannula, the widths of the outer surfaces and inner surfaces being substantially greater than the widths of the side surfaces;

at least one sensor to monitor the temperature of the pathological tissue effected by the RF energy;

at least one cutting instrument to create a surgical pathway for implantation of the inflatable bone tamp; and a liquid pumping system configured to be connected to the inflatable bone tamp.

17. A system as recited in claim 16, comprising more than one inflatable bone tamp with each having a size different than the other inflatable bone tamps.

18. A system as recited in claim 16, comprising more than one inflatable bone tamp with each having a shape different than the other bone tamps.

19. A system as recited in claim 16, comprising more than one cannula of various sizes.

* * * * *